United States Patent
Secrest et al.

(10) Patent No.: US 7,108,661 B2
(45) Date of Patent: Sep. 19, 2006

(54) METHOD AND COLLECTION DEVICE FOR BARRETT'S ESOPHAGUS CELLS

(75) Inventors: Dean J. Secrest, Concord, OH (US); Marlin Younker, Waite Hill, OH (US)

(73) Assignee: United States Endoscopy Group, Inc., Mentor, OH (US)

( * ) Notice: Subject to any disclaimer, the term of this patent is extended or adjusted under 35 U.S.C. 154(b) by 564 days.

(21) Appl. No.: 10/275,336

(22) PCT Filed: May 7, 2001

(86) PCT No.: PCT/US01/14568

§ 371 (c)(1), (2), (4) Date: Nov. 6, 2002

(87) PCT Pub. No.: WO01/85032

PCT Pub. Date: Nov. 15, 2001

(65) Prior Publication Data

US 2003/0208134 A1    Nov. 6, 2003

(51) Int. Cl.
*A61B 10/00* (2006.01)

(52) U.S. Cl. ...................... 600/569; 600/562

(58) Field of Classification Search ............. 15/104.16, 15/104.17–104.19, 104.2; 600/562, 569–572; 604/1, 910; 606/196, 200
See application file for complete search history.

(56) References Cited

U.S. PATENT DOCUMENTS

| 4,301,797 A | 11/1981 | Pollack |
| 4,324,262 A | 4/1982 | Hall |
| 4,617,015 A | 10/1986 | Foltz |
| 4,921,484 A | 5/1990 | Hillstead |
| 4,946,440 A * | 8/1990 | Hall ...................... 604/164.09 |
| 4,966,162 A * | 10/1990 | Wang ........................ 600/563 |
| 5,314,409 A * | 5/1994 | Sarosiek et al. ....... 604/101.03 |
| 5,370,653 A * | 12/1994 | Cragg ........................ 606/170 |
| 5,533,516 A | 7/1996 | Sahatjian |
| 5,738,109 A | 4/1998 | Parasher |
| 6,035,229 A | 3/2000 | Silverstein et al. |

FOREIGN PATENT DOCUMENTS

| GB | 1547328 | * 6/1979 |
| WO | WO 99/42160 | 8/1999 |

OTHER PUBLICATIONS

International Search Report dated Nov. 7, 2001.

* cited by examiner

*Primary Examiner*—Max F. Hindenburg
*Assistant Examiner*—Michael Apanius
(74) *Attorney, Agent, or Firm*—Calfee, Halter & Griswold LLP

(57) ABSTRACT

A method and apparatus for obtaining esophageal cells for diagnostic purposes. A distal end of a support body is inserted in a patient's stomach via the esophagus and mouth. A balloon at the distal support body end is inflated. The support body is withdrawn until the balloon engages the sphincter. A support body location is marked that is a predetermined distance from the patient's dental arch. The balloon is deflated and the support body is withdrawn so that the marked location is adjacent the patient's dental arch. The support body is withdrawn a second predetermined distance and a second support body location is marked. A cell collecting element is deployed from within the distal end of the support body. The support body is reciprocated with the cell collecting element deployed so that cells from the esophagus are deposited on the cell collecting element.

7 Claims, 5 Drawing Sheets

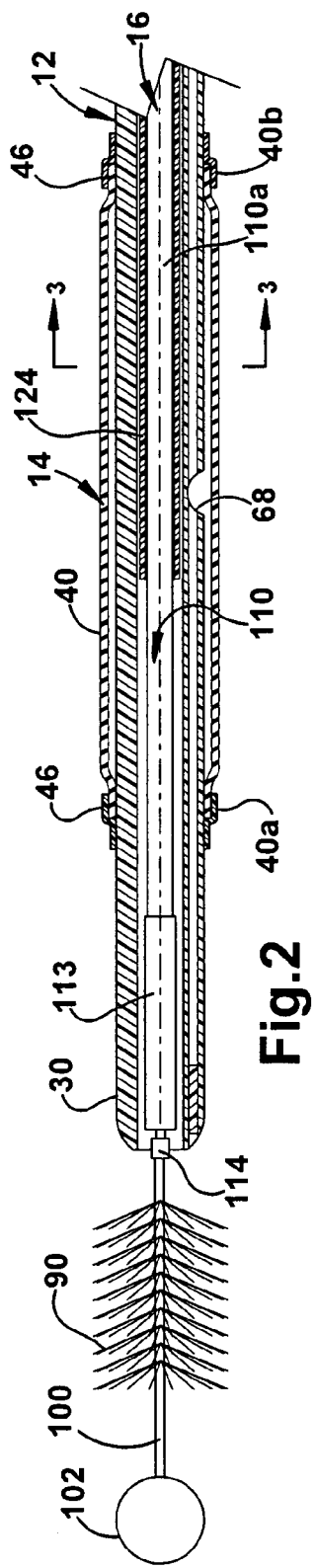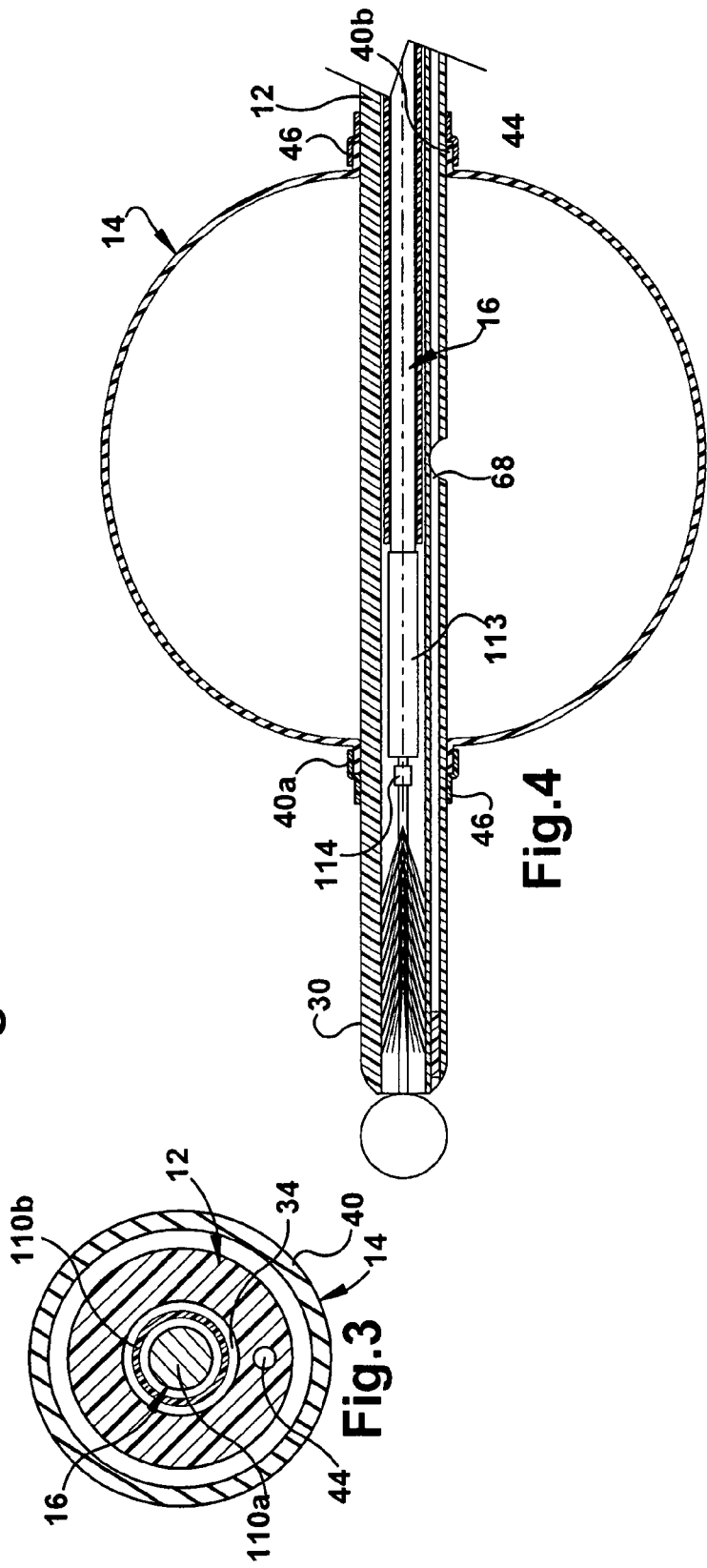

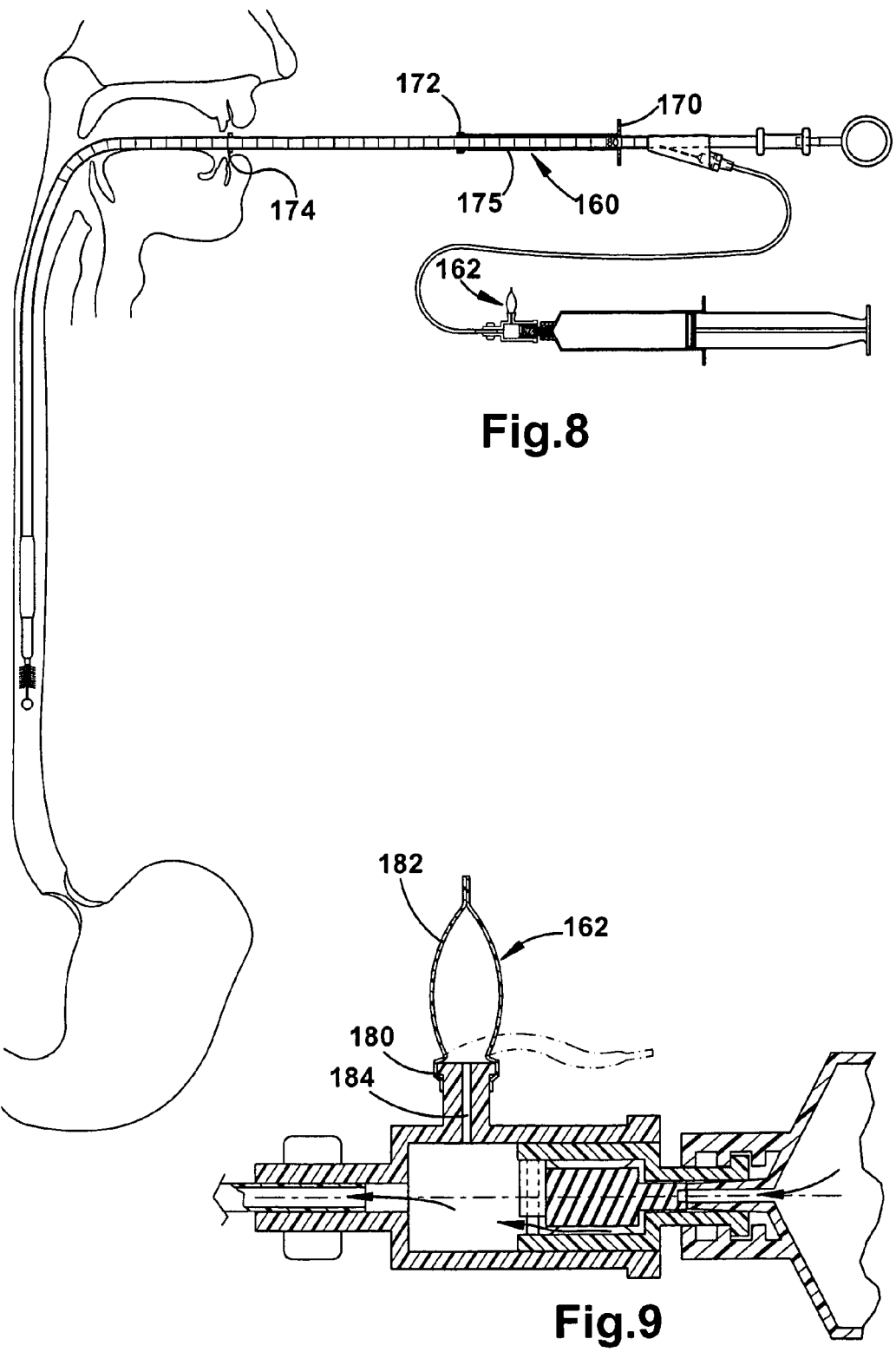

METHOD AND COLLECTION DEVICE FOR BARRETT'S ESOPHAGUS CELLS

FIELD OF THE INVENTION

The present invention relates to collecting cells for cytological examination and more particularly to a method and device for collecting Barrett's esophagus cells for cytological study.

BACKGROUND OF THE INVENTION

Barrett's esophagus is a condition in which cells lining the esophagus near the entrance to the stomach become abnormal due to exposure to stomach acid. Barrett's esophagus typically extends about 8 cm away from the stomach entrance. The condition is often a precursor of esophageal cancer, so detection of abnormal cells indicating not only esophageal cancer, but also Barrett's esophagus, is important.

Barrett's esophagus and esophageal cancer are diagnosed by visually inspecting the esophagus lining, collecting cells from the esophagus lining and subjecting them to cytological examination. Procedures for collecting the cells have been such that diagnosing Barrett's esophagus or esophageal cancer was quite expensive. When the esophagus lining was visually inspected, an endoscope was employed and the patient was anesthetized for the process. The visualization process enables the physician to determine the location of the cells in question. A cell collection device may then be inserted through the endoscope and engaged with the esophagus lining in the areas where the cells in question have been located.

Various devices for collecting cells have been proposed. Among these have been inflatable balloon-like elements that have been inserted into the esophagus through the endoscope, inflated and rubbed on the lining to collect the cells. The balloons were deflated for removal. These devices have not been completely satisfactory in collecting adequate numbers of cells for examination. Brushes have also been used to collect cells. Brushes have been effective to collect sufficient numbers of cells, but have been constructed so that they brushed the entire length of the esophagus during removal. This has been undesirable because cells collected from the region of the esophagus near the stomach entrance have been dislodged from the brush during extraction of the brush from the esophagus. Dislodging such cells not only reduced the number of cells available for examination but also deposited the cells in regions of the esophagus where abnormal cells did not exist.

The present invention provides a new and improved method and apparatus for collecting cells from the esophagus for cytological examination wherein the process of collecting the cells is relatively inexpensive, does not require use of an endoscope, or the like, for locating the region of the esophagus from which cells are to be obtained and wherein regions of the esophagus remote from the stomach are not contacted by cell collection devices.

SUMMARY OF THE INVENTION

The present invention provides a method of obtaining esophageal cells for diagnostic purposes comprising inserting the distal end of a flexible support body into a patient's stomach via the esophagus and mouth so that the proximal support body end projects from the mouth, expanding an expandable member at the distal support body end and withdrawing the support body until the expanded member engages the sphincter at the stomach entrance, marking a support body location that is a predetermined distance from the patient's dental arch when the expanded member engages the sphincter at the stomach entrance, contracting the expanded member and withdrawing the support body so that the marked location is adjacent the patient's dental arch, withdrawing the support body a second predetermined distance and marking a second support body location that is adjacent the patient's dental arch, deploying a cell collecting element from the distal end of the support body so that the cell collecting element is disposed in the esophagus within the predetermined distance from the sphincter, reciprocating the support body through the second predetermined distance with the cell collecting element deployed so that cells from the esophagus within the second predetermined distance from the sphincter are deposited on the cell collecting element, conditioning the cell collecting element so that it does not engage the esophagus wall, and, withdrawing the support body from the patient.

A cytology device embodying the invention comprises a flexible support body, a stomach sphincter locating system, a cell collecting system, and marker elements adjustably movable along the support body by the physician.

The support body comprises a flexible support body having a distal end that is insertable into a patient's stomach via the esophagus and a proximal end that projects from the patient's mouth when the distal end is in the patient's esophagus. The disclosed stomach sphincter locating system comprises a balloon attached to the support body at the distal end, an inflation unit at the proximal support body end and an inflation-deflation channel communicating the balloon with the inflation unit. The disclosed cell collecting system comprises a brush disposed at the distal support body end, a brush actuator extending from the brush to the proximal support body end, and a handle connected to the brush actuator for shifting the brush axially relative to the support body between a retracted position where the brush is disposed within the support body and a deployed position where the brush is disposed beyond and adjacent the distal end.

Additional features and advantages will become apparent from the following description of an illustrated embodiment made with reference to the accompanying drawings which from part of the specification and wherein:

BRIEF DESCRIPTION OF THE DRAWINGS

FIG. 2 is an enlarged fragmentary cross sectional view of part of the device of FIG. 1;

FIG. 3 is a cross sectional view seen approximately from the plane indicated by the line 3—3 of FIG. 2;

FIG. 4 is a view similar to that of FIG. 2 with parts in different operating conditions;

DESCRIPTION OF THE BEST MODE CONTEMPLATED FOR PRACTICING THE INVENTION

Figure 1:
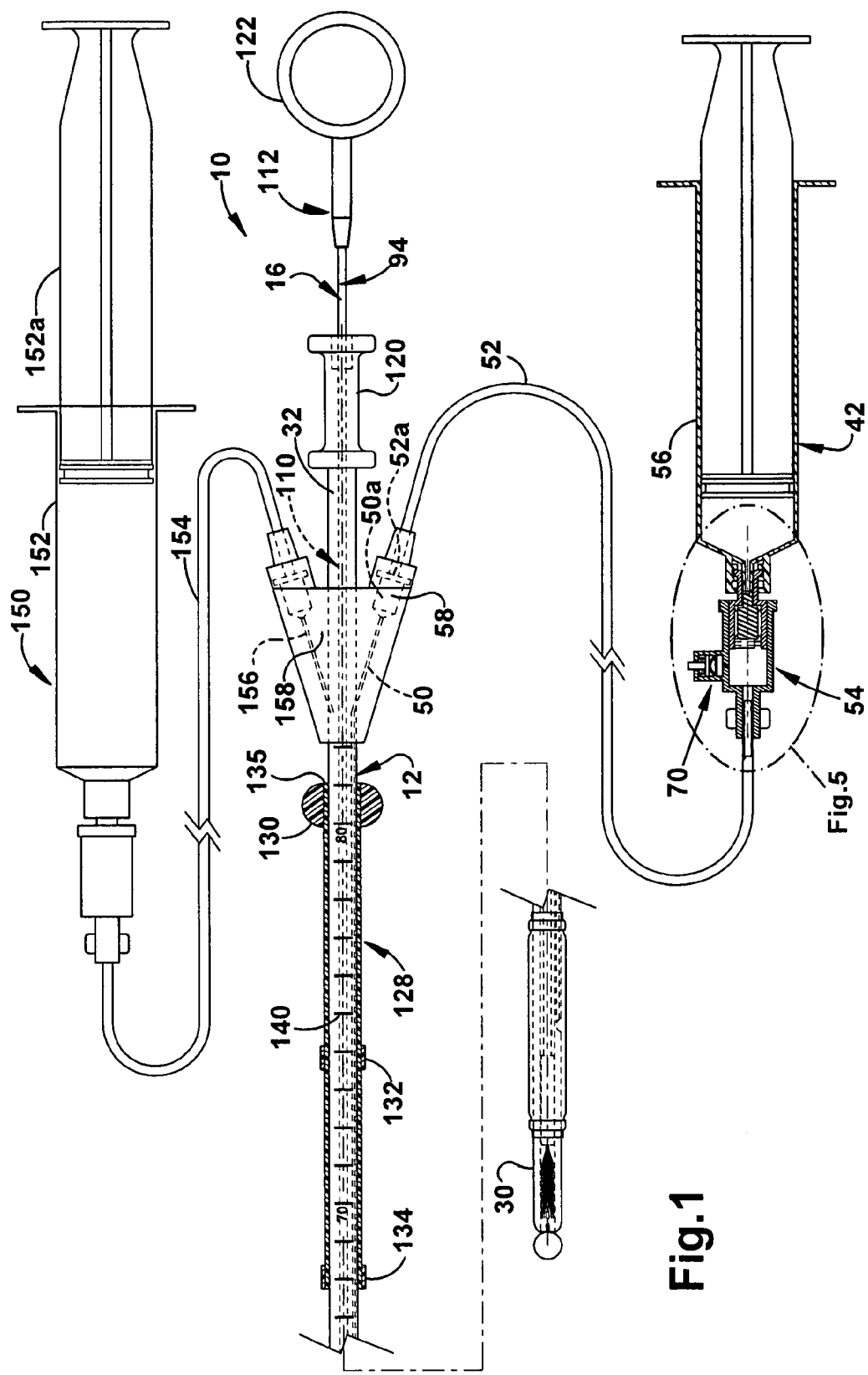
FIG. 1 is a fragmentary elevational view of a cytology device embodying the present invention with parts shown in cross section.
Figure 6:
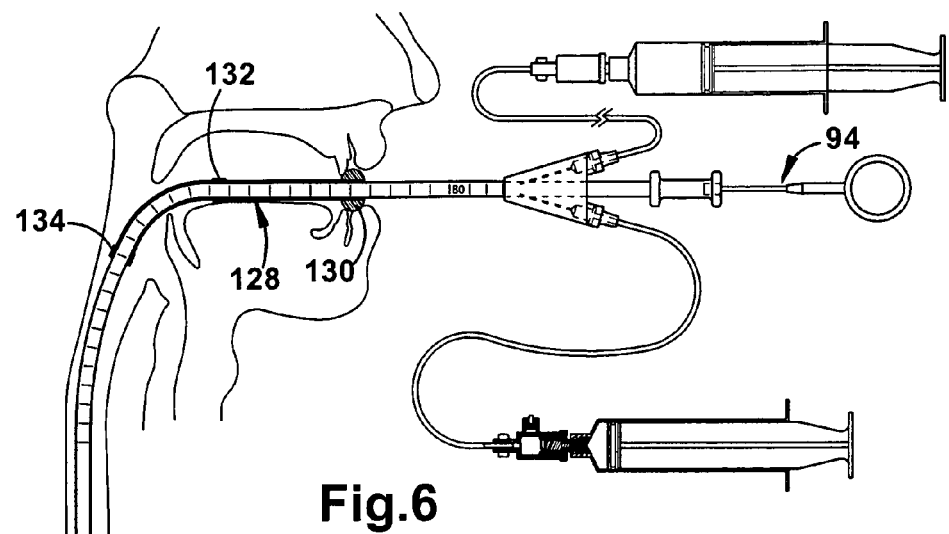
FIG. 6 is a view showing the device inserted in the stomach of a patient.

A cytology device 10 constructed according to the invention is illustrated by FIGS. 1–5 as comprising a flexible support body 12, a stomach sphincter locating system 14, and a cell collecting system 16. The support body is an elongated flexible member that is inserted into a patient's stomach via the esophagus and mouth. The stomach sphincter location system 14 is supported by the support body 12 and serves to locate the sphincter relative to the support body. The cell collecting system 16 is carried by the support body 12 and deployed to collect cells from a region of the esophagus that extends a short distance from the stomach entrance toward the patient's mouth. When cells have been collected the device 10 is withdrawn from the patient without further contact between the cell collection system and the esophagus wall.

The illustrated support body 12 is an elongated, flexible member that supports the location system 14 and the cell collecting system 16. The body length is sufficient that one body end, the distal end, 30 can be inserted in a patient's mouth and passed through the esophagus into the stomach while the other, proximal, end 32 remains outside the patient's body accessible to the physician. The flexible nature, and diametrical extent, of the support body 12 are such that it may be inserted with minimal patient discomfort.

The illustrated support body 12 is formed by a flexible plastic tube having a generally cylindrical configuration that defines a central passage 34 (see FIG. 3). The illustrated body 12 has an outside diametrical extent of around 0.25 in. The systems 14, 16 are operated by the physician from the proximal tube end 32 with the location and collection functions performed at the distal tube end 30. The illustrated body is formed from a clear plastic material—such as pvc, silicone, urethane, or a thermoplastic elastomer like c-flex—so the tube contents are visible from outside the tube, but the body may be formulated so that it is opaque if desired.

The stomach sphincter locating system 14 comprises an expandable member 40 attached to the support body at the distal end 30, and an expander system 42 at the proximal body end 32 by which the physician can control expansion of the member 40. When the body 12 has been inserted in the patient so that the expandable member 40 is located within the stomach, the member 40 is expanded to a diametrical size that is too great to pass through the stomach sphincter. The body 12 is then withdrawn until the member 40 engages the sphincter and further withdrawal of the body is strongly resisted. This enables locating the sphincter relative to the patient's body, as well as locating the region of the esophagus wall immediately above the sphincter, where cells to be examined are found. The physician then contracts the member 40 to its initial diametrical size and withdraws the distal end of the body 12 from the stomach into the esophagus above the sphincter.

In the illustrated device the expandable member 40 is formed by a balloon. The balloon 40 is formed by a thin cylindrical sheath of elastomeric material—such as c-flex—that is hermetically attached to the body 12 at its opposite ends 40a, 40b. The balloon 40 communicates with the expander system 42 via an inflation-deflation channel 44 that extends between the balloon and the proximal body end. As illustrated, the body 12 extends a short, predetermined distance beyond the distal balloon end 40a.

In the device illustrated by the drawings, the balloon is attached to the body by plastic sleeves 46 that extend over the balloon ends and along the body exterior for a short distance from each respective balloon end. The sleeves 46 are shrunk into hermetic engagement with both the balloon ends and the body 12 to seal the balloon in place at the distal body end. In the illustrated device an adhesive is applied to the sleeves so that they are bonded to the body 12 and the balloon 40. The sleeves 46 are illustrated as fashioned from heat shrinkable Mylar, but they can be fashioned from any suitable material that is capable of being shrunk into elastic engagement with an underlying support member either by the application of heat, chemical action or other means. Furthermore, the balloon may be attached to the body by other suitable or conventional modes of hermetic bonding.

The illustrated expander system 42 operates to inflate and deflate the balloon 40 under the physician's control. The illustrated system 42 comprises a blunt needle 50 that extends into and communicates with the inflation-deflation channel 44, an inflation hose 52 hermetically joined to the needle 50, a check valve 54 that is joined to the hose 52 distal the needle 50, and a syringe 56 for inflating and deflating the balloon via the valve 54, and the channel.

The blunt needle 50 is a conventional needle having a tubular cannula section that extends through the body wall into the channel 44 and an enlarged end fitting 50a. In the illustrated device the needle 50 is hermetically secured to the body 12 by friction, glue and a heat shrink urethane adhesive 58 that is wrapped around the body and needle and, when heated, flows to seal the needle-body juncture.

The hose 52 has an end fitting 52a that screws onto the needle fitting 50a and is hermetically bonded in place to the needle fitting by a suitable adhesive material. The opposite hose end is hermetically joined to the valve 54.

Figure 5:
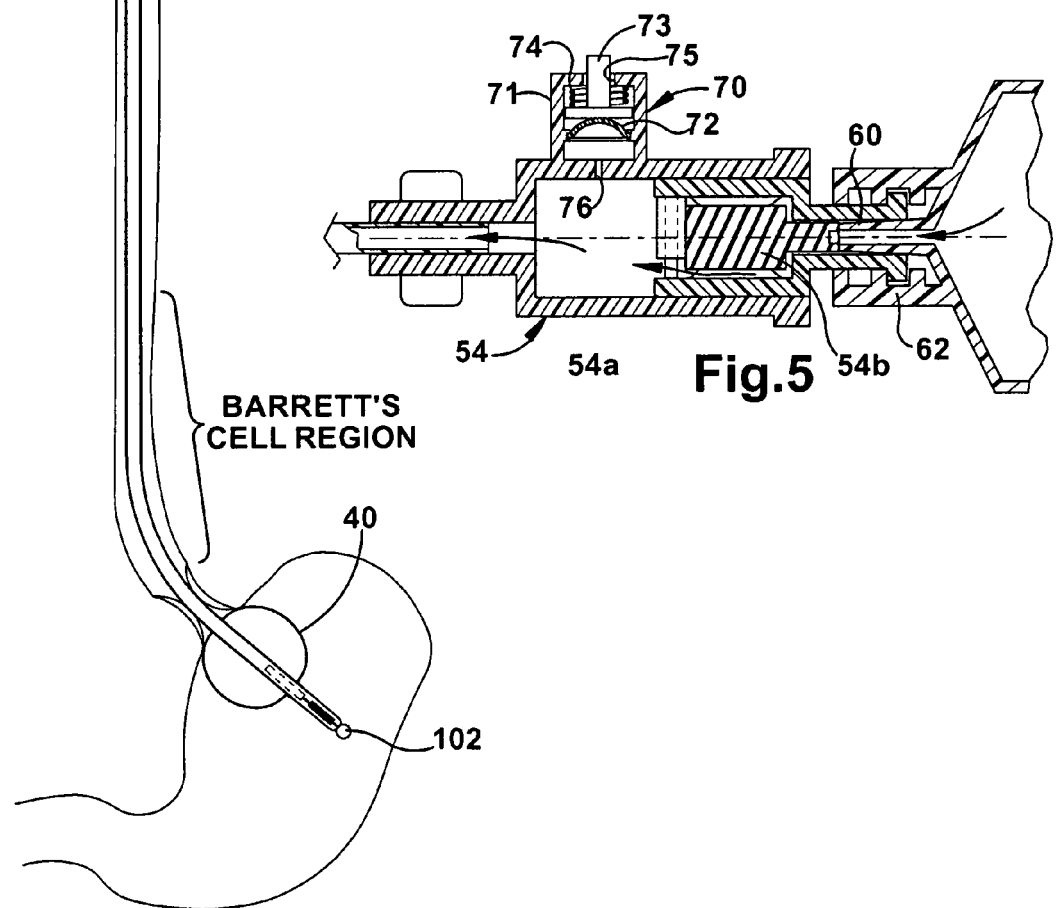
FIG. 5 is an enlarged view of part of the cytology device within the line 5 of FIG. 1.

As illustrated by FIG. 5, the valve 54 is a conventional check valve having a tubular valve body 54a and a resiliently compressible valve member 54b that seats in the valve body to prevent flow through the body to the hose 52. The proximal end of the valve body is formed with a central port 60 that is aligned with the valve member. The valve member is normally seated over the port to block flow through the hose 52.

The illustrated syringe 56 is detachably connectable to the valve 54 by a suitable coupling structure. The syringe 56 is constructed with a threaded discharge end 62 that screws onto the valve body 54a. When the syringe is fully screwed onto the valve body, the discharge end 62 engages, resiliently depresses, and unseats the valve member 54b enabling flow through the hose 52. The syringe contains atmospheric air that is forced through the valve 54 for inflating the balloon when the physician advances the syringe plunger. The balloon is deflated by the physician retracting the syringe plunger. The plunger is illustrated as provided with a thumb pad that enables the physician to manipulate it. When the balloon is not being used, it is deflated and the syringe is unscrewed from the valve body. The valve recloses and assures that the balloon remains fully deflated.

In the illustrated device 10 the body 12 is an extruded plastic tube with the inflation-deflation channel 44 formed by a narrow passage that is extruded into the body wall so that it coextends with the central body passage 34. The body wall is notched in radial alignment with the passage 44 at the location where the blunt needle is to be positioned. The notch extends through the body wall sufficiently that the passage 44 is accessible and the needle can be inserted directly into the passage.

A small hole 68 is formed in the body wall within the balloon 40 that extends to the passage 44 to enable the balloon to be inflated and deflated via the passage 44. The end of the passage 44 that opens at the distal body end is plugged by a suitable urethane adhesive material, although other plugging techniques can be employed. Although the device 10 is illustrated as provided with an inflation-deflation channel 44 formed in the wall of an extruded body 12, alternative constructions are possible, including a separate inflation-deflation tube that coextends with the body 12.

The device 10 of FIGS. 1–7 is illustrated as comprising an indicator mechanism 70 for signaling the physician when the stomach sphincter locating system is enabled. In the embodiment referred to, the mechanism 70 provides a signal in response to inflation and deflation of the balloon. The mechanism 70 illustrated in FIGS. 1–7 produces a visual indication when the balloon 40 is inflated. FIGS. 1–7 show the mechanism 70 as comprising a tubular housing 71 formed integrally with the check valve body 54a, a flexible diaphragm 72 sealed within the housing 71, a pop-up button 73 confined within the housing 71, and a spring 74 that reacts between the button and the housing to bias the button against the diaphragm 72. The housing end remote from the valve body 54a defines an opening 75 aligned with the button 73 so that the button can project from the housing 71 through the opening 75. The housing end proximal the valve body 54a is illustrated as communicating with the valve housing 54a via a small diameter bleed hole 76 that throttles flows of air between the housing 71 and the valve body 54a.

When the balloon 40 is inflated, air from the valve body 54a bleeds into the housing 71 until the pressure in the housing 71 is sufficient to force the diaphragm 72 toward the button against the force of the spring 74. The diaphragm shifts the button so that it projects through the opening 75, thus signaling that the balloon is inflated. Because the flow through the bleed hole 76 is restricted, the button projects from the housing 71 after a short delay period.

When the syringe plunger is retracted to deflate the balloon, air from within the housing 71 bleeds to the valve body 54a through the hole 76, gradually reducing the pressure behind the diaphragm. As the pressure behind the diaphragm reduces, the button 73 is forced against the diaphragm by the spring 74 and by atmospheric air pressure ambient the device 10 so that the button retracts into the housing 71. This retraction signals that the balloon is deflated. The delay period before the button retracts insures that the balloon is fully deflated before the physician attempts to remove the distal end of the device 10 from the patient's stomach. While a balloon 40, channel 44, and inflation-deflation unit 42 are illustrated, other kinds of expandable members and expansion units may be employed. For instance, radially shiftable fingers may be positioned at the distal body end and actuated between radially extended and retracted positions by an operating cable extending through the body 12 to the proximal body end and accessible to the physician. Any suitable or conventional expandable member and expansion unit may be employed.

The cell collection system 16 is constructed and arranged for collecting cells from the region of the esophagus wall that is under investigation without contacting any other part of the esophagus wall. The illustrated cell collection system comprises a cell collecting member 90 that is deployed in a cell collecting condition where it engages the esophagus wall and dislodges cells that adhere to the member 90. After collecting the cells the physician can actuate the member 90 so that it no longer contacts the esophagus wall as the body 12 is withdrawn from the esophagus. Consequently the collection member does not contact the esophagus wall region beyond that where the cells are to be collected and cells that have been collected by the member 90 are not deposited on the esophagus wall as the body 12 is removed.

In the illustrated cell collection system 16 the member 90 is formed by a cell collecting brush that is supported at the distal body end and an actuator 94 for operating the brush between its operative conditions. The brush 90 is constructed and arranged so that it is carried within the distal end of the body 12 as the body is inserted and removed from the patient yet can be deployed from the distal body end for brushing cells from the esophagus wall when desired.

The illustrated brush comprises a central body 100 formed by a twisted wire cable, bristles that are wound in the body wires and project radially from the body, and a bead-like tip 102 fixed to the projecting end of the body 100 to assure that the distal end of the device 10 smoothly engages the patient's alimentary canal without abrading or otherwise causing damage. The illustrated bristles are formed from nylon and the bead tip is a suitable non-reactive plastic.

The actuator 94 comprises a flexible link 110 extending to the brush 90 from the proximal body end 32 and a handle assembly 112 that is located at the proximal body end for enabling the physician to deploy and retract the brush 90 by pushing and pulling the link 110. The link 110 is illustrated as comprising a cable 110a, formed by twisted wires, that extends through the central passage 34 and a sheath-like tube 110b that surrounds the cable. The cable 110a is fixed to the brush 90 by a coupling element 113 that is crimped to both the brush body 100 and the cable 110a.

In the device illustrated by FIGS. 1–7 the sheath 110b extends within the central passage 34. The sheath 110b is illustrated as a thin walled tube that loosely surrounds the cable link and "floats" within the passage 34. The sheath is formed from Teflon, or some other low friction material, that enables the cable link to shift easily in the axial direction along the sheath. The sheath is relatively stiff and rather closely surrounds the cable link for supporting the cable against any tendency to buckle as it pushes the brush 90 out of the body end.

In the illustrated device 10, the central brush body 100 is formed by relatively fine wires that are severed by shears after cells have been harvested. The severed brush is deposited in a sample container for later cytological examination. In order to facilitate proper removal of the brush, a color coded band 114 is fixed to the body 100 between the coupling element 113 and the brush bristles. The band 114 indicates where to sever the brush so that the central body 100 is severed, not the cable 110a, which is thick and might otherwise damage the severing shears.

The handle assembly 112 comprises a guide fitting 120 fixed to the proximal body end, a thumb ring member 122 operable by the physician when the brush is deployed and retracted, and a cable support sleeve 124 fixed to the cable and the thumb ring for guiding the cable movement through the guide fitting 120 as well as prevent cable buckling that would other wise occur when the proximal cable end projects from the guide fitting 120 end as the brush is being deployed. The sleeve 124 is a rigid element that is telescoped over, and fixed to, the cable.

The illustrated thumb ring and guide fitting are constructed so that they are wedged together and frictionally maintained in predetermined positions relative to each other when the brush 90 is fully deployed so that the dimensional relationship between the brush and the proximal end of the body 12 is maintained constant as the device 10 is manipulated. The guide fitting has a central bore that forms a slip-fit relationship with the sleeve 124 when the brush is deployed. The close fit between the guide fitting and sleeve 124 effectively seals against the flow of air between them. The handle assembly 112 can be of any suitable or conventional construction and is not described in further detail.

When the device 10 is inserted in the patient it is essential to know where the brush 90 is in relation to the patient's esophagus when cells are being collected. In order to minimize the cost and complexity of the procedure it is advantageous to be able to accurately determine the brush position without using x-ray imaging techniques and without endoscopically identified landmarks or measurements. The device 10 enables the physician to accomplish these ends in a simple and effective way.

When the device 10 is initially inserted into the patient's stomach, the balloon is inflated and the device withdrawn until resistance is encountered. At this juncture, the position of the balloon is known to be just within the patient's stomach in engagement with the sphincter. With the device 10 so positioned, the location on the body 12 that is aligned with the patient's dental arch—i.e. the upper front teeth or gum—is marked. The distance between the proximal end of the balloon and the brush, when deployed, is a known quantity. The physician marks the body location that is spaced from the first mark a distance that corresponds to the dimension between the balloon proximal end and the deployed brush, plus a distance that corresponds to an assumed length of the sphincter. When the second, marked body location is aligned with the patient's dental arch, the physician is substantially certain that the deployed brush is positioned at the distal end of the esophagus.

The location of Barrett's cells in the esophagus is typically limited to the esophagus wall extending about eight centimeters from the esophagus distal end. Accordingly, the body 12 is marked at a third location spaced eight centimeters from the second location.

At this juncture the body 12 is positioned so that the second location is aligned with the dental arch and the brush is deployed. The body 12 is withdrawn until the third location is aligned with the dental arch and the motion is repeated several times so that the Barrett's cell region of the esophagus is thoroughly brushed. The brush is then retracted into the body 12 and the device 10 is removed from the patient. In the device illustrated by FIGS. 1–7 a marker unit 128 is used by the physician to locate the region of the esophagus wall from which cells are to be collected. The marker unit 128 comprises marker elements 130, 132, and 134 that are adjustably positionable on the support body to provide visual indications of support body location relative to the esophagus and respectively mark the first, second, and third body locations that are referred to above. The device 10 is illustrated with the marker elements 130, 132, 134 each located on a marker member 135 that is movable along the body 12 by the physician. The illustrated marker member 135 is a flexible, transparent tube that surrounds and frictionally engages the body 12. The member 135 may be positioned where desired on the body 12 and is frictionally maintained in the adjusted position.

The marker element 130 is illustrated as formed by a bead-like member that surrounds, and is fixed to, the body member 135. The marker 130 is located on the end of the member 135 proximal to the handle assembly 112. The element 130 engages the patient's front upper teeth or gum (the dental arch) to mark the first body location. The elements 132, 134 respectively mark the second and third body locations. Because the elements 132, 134 are stationed on the member 135, the second and third body locations are marked when the first location is established.

Each marker element 132, 134 is illustrated as formed by a band or ring that encircles, and is fixed in place on, the member 135. The bands are illustrated as shrunk fit in place, but they can be of any appropriate construction and attached in other ways. They can also be formed by indicia imprinted directly on the member 135 by the supplier of the device or by the physician during the procedure.

In the illustrated device 10, the body 12 is provided with indicia, indicated generally at 140, that may be used to aid in positioning the marker elements as well as to enable brushing accurately located areas of the esophagus that are beyond the usual location of Barrett's cells. The illustrated indicia 140 are formed on the outside surface of the body 12 using a darkly opaque substance. The indicia are spaced apart by a predetermined number of millimeters. The indicia 140 are dark so they are relatively easily seen, particularly where the body 12 and the member 135 are constructed from substantially transparent plastic materials.

The illustrated cell collection system 16 includes an optional cell recovery system 150 for assuring that some cells which might otherwise be lost are recovered for analysis. After the esophagus wall has been brushed, the brush 90 is retracted into the body 12 so that the device 10 may be removed without brushing the esophagus wall above the Barrett's cell region. When the brush is retracted, the bristles engage the distal body end as they slide through the aperture at the distal end of the body 12. Material carried by the bristles, including cells that have been harvested, may become dislodged from the bristles, deposited on the distal end of the body 12 as the bristles pass by, and lost when the body is withdrawn from the esophagus. In the illustrated device 10, the material removed from the brush 90 during retraction is delivered into the body by the cell recovery system 150 and preserved against loss.

Referring to the device illustrated by FIGS. 1–7, the cell recovery system 150 comprises a syringe assembly 152, a hose 154 detachably connected to the syringe assembly, a blunt needle 156 communicating between the hose 154 and the central body passage 34, and a fitting 158 that secures the needle 156 to the body 12. When the brush 90 is retracted into the end of the body 12, the plunger 152a of the syringe assembly 152 is quickly withdrawn, creating a vacuum pressure in the passage 34. Material dislodged from the brush during its retraction and clinging to the tip end of the body is sucked into the passage 34 when the vacuum pressure is created.

In the illustrated device 10 the syringe assembly 152, hose 154, needle 156, and fitting 158 may all be of the same construction as the needle 50, hose 52 and syringe 56 described above. The syringe assembly 152 is constructed so that it can be detached from the hose when not in use. It should be noted that the snug fit between the guide fitting 120 and the support sleeve 124 provides a seal and blocks the inrush of atmospheric air that would otherwise occur when the vacuum is established in the passage 34.

FIGS. 8 and 9 of the drawings illustrate a device 10 that is constructed using an alternative marker unit 160 and an alternative inflation-deflation signaling mechanism 162.

The marker unit 160 comprises marker elements 170, 172, and 174 that are adjustably positionable on the support body to provide visual indications of support body location relative to the esophagus and respectively mark the first, second, and third body locations that are referred to above. The device 10 is illustrated with the marker elements 170, 172, each located on a marker member 175 that is movable along the body 12 by the physician. The illustrated marker member 175 is a flexible, transparent tube that surrounds and frictionally engages the body 12. The member 175 may be positioned where desired on the body 12 and is frictionally maintained in the adjusted position.

The marker element 170 is illustrated as formed by a dental arch engaging flange at one end of the member 175 while the marker element 172 is formed by printed indicia at the opposite end of the member 175. The length of the member 175 corresponds to the distance from the proximal balloon end to the deployed brush plus an amount corresponding to the length of the sphincter between the patient's stomach and esophagus. When the marker flange 170 is positioned so it engages the patient's dental arch, the marker 172 is positioned at the second location on the body 12. The physician needs only to adjust the position of the marker element 174 as desired to the third location on the body 12 before collecting the cells.

Figure 7:
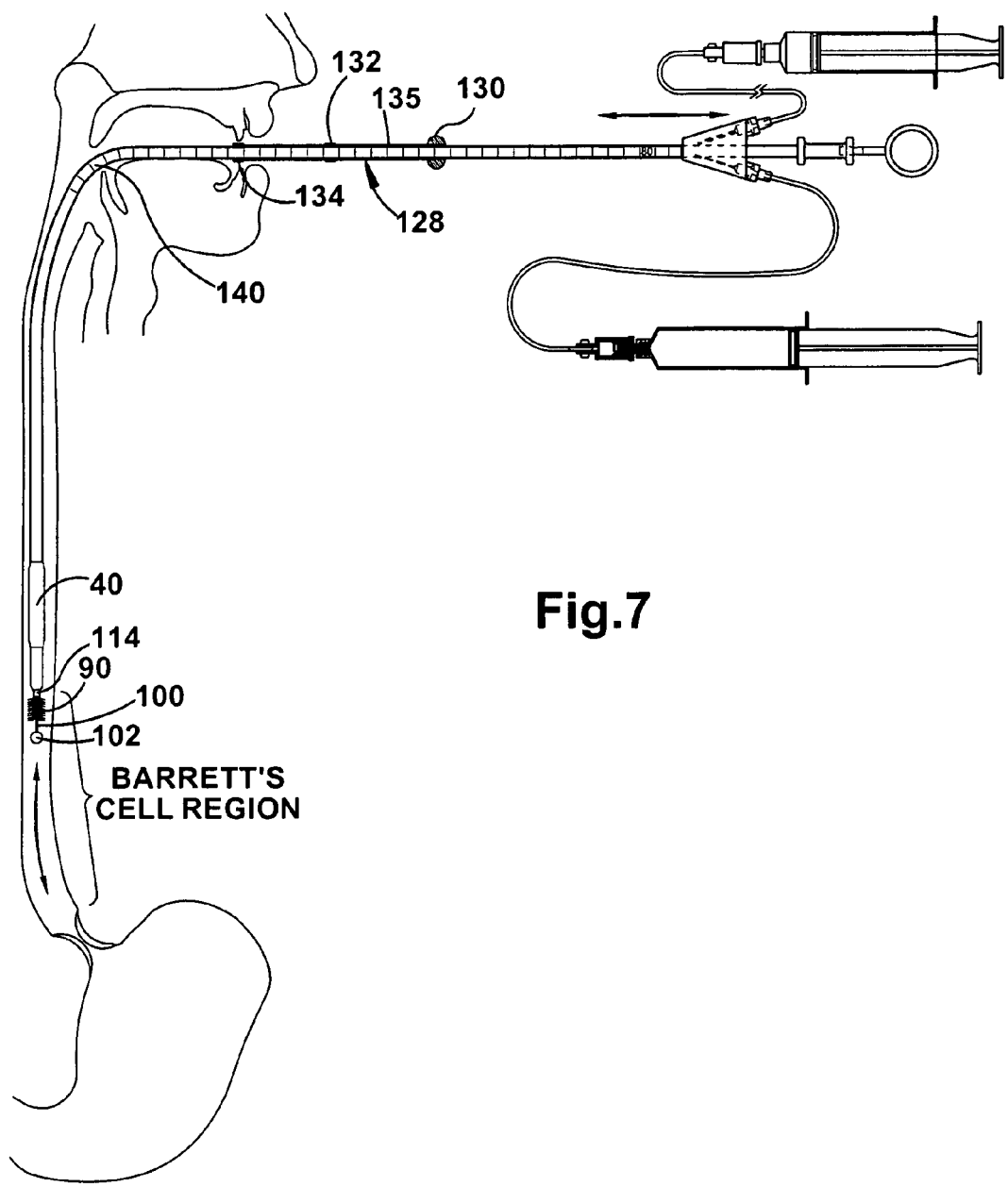
FIG. 7 is a view similar to that of FIG. 6 illustrating the device conditioned for collecting cells for examination; and, FIG. 8 is a view similar to FIG. 6 illustrating a modification of the device of FIG. 1; and, FIG. 9 is an enlarged view of a portion of the device of FIG. 8 with a part in an alternative position.

The marker element 174 that is illustrated in FIG. 7 is formed by a resilient rubber-like O-ring that is frictionally engaged with the body 12 and movable as desired along the body by the physician. Because the body 12 carries indicia 140 indicating length, the physician can locate the element 174 where desired to determine the brush stroke length.

The marker element 174 that is illustrated in FIG. 8 is formed by a resilient rubber-like O-ring that is frictionally engaged with the body 12 and movable as desired along the body by the physician. Because the body 12 carries indicia 140 indicating length, the physician can locate the element 174 where desired to determine the brush stroke length.

The inflation signaling mechanism 162 signals the physician when the stomach sphincter locating system is enabled. The illustrated mechanism provides a visual indication when the balloon 40 is inflated or deflated. FIGS. 8 and 9 show the mechanism 162 as comprising a tubular housing 180 formed integrally with the check valve body 54a, and an inflation indicator element 182 secured to the housing 180.

The illustrated housing 180 projects from a side of the check valve body 54a. The housing end proximal the valve body is sealed to the valve body and a flow restricting vent hole 184 communicates the valve body 54a with the interior of the housing 180. The inflation indicator element 182 is fixed to the housing end remote from the valve body 54a.

The inflation indicator element 182 is illustrated as a thin-walled, flexible plastic tube that communicates with the housing 180 and inflates and deflates as the balloon 40 is inflated and deflated. The illustrated element 182 has its end proximal the housing sealed about an opening in the distal housing end. The element end remote from the housing 180 is sealed closed. The illustrated indicator element is constructed from a plastic film material that is supple but relatively non-resilient compared to the material forming the balloon 40.

When the balloon begins to inflate, inflation air bleeds through the vent hole 184 so that the element 182 gradually inflates. When fully inflated, the element 182 straightens, becomes erect, and projects away from the housing 180 to provide a visual indication of the balloon condition (FIG. 8). The element 182 has a small internal volume compared to that of the balloon 40 and the film material from which it is constructed is nonresilient compared to the balloon material so that both the element 182 and the balloon 40 are fully inflated.

When the balloon begins to deflate, the air is drawn from the element 182 through the vent hole 184. Because of its flaccidity, the element 182 collapses and crumples, indicating that the balloon is deflated. In the illustrated device 10 the vent hole 184 throttles the air flow to and from the element 182 so that the balloon is either fully inflated or fully deflated when the element signals the balloon condition.

While several embodiments of the invention have been illustrated and described in considerable detail, the invention is not to be considered limited to the precise constructions disclosed. Various adaptations, modifications, and uses of the invention may occur to those skilled in the business to which the invention relates. The intention is to cover all such adaptations, modifications, and uses coming within the spirit or scope of the appended claims.

What is claimed is:

1. A method of obtaining esophageal cells for diagnostic purposes comprising:
   a. inserting the distal end of a flexible support body into a patient's stomach via the esophagus and mouth so that the proximal support body end projects from the mouth;
   b. expanding an expandable member at the distal support body end and withdrawing the support body until the expanded member engages the sphincter at the stomach entrance;
   c. marking a support body location that is a predetermined distance from the patient's dental arch when the expanded member engages the sphincter at the stomach entrance;
   d. contracting the expanded member and withdrawing the support body so that the marked location is adjacent the patient's dental arch;
   e. withdrawing the support body a second predetermined distance and marking a second support body location that is adjacent the patient's dental arch;
   f. deploying a cell collecting element from the distal end of the support body so that the cell collecting element is disposed in the esophagus within the second predetermined distance from the sphincter;
   g. reciprocating the support body through the second predetermined distance with the cell collecting element deployed so that cells from the esophagus within the second predetermined distance from the sphincter are deposited on the cell collecting element;
   h. conditioning the cell collecting element so that it does not engage the esophagus wall; and
   i. withdrawing the support body from the patient.

2. The method claimed in claim 1 wherein the first step of marking the support body comprises frictionally securing a first marker element to the support body at said first support body location.

3. The method claimed in claim 1 wherein the second step of marking the support body comprises frictionally securing a second marker element to the support body at said second support body location.

4. The method claimed in claim 1 wherein the first step of marking the support body comprises frictionally securing a first marker element to the support body at first support body location and the second step of marking the support body comprises frictionally securing a second marker element to the support body at said second support body location.

5. The method claimed in claim 4 wherein marking the support body at said first support body location further comprises frictionally securing a third marker element to the support body in alignment with the patient's dental arch when a balloon is located at the patient's sphincter and thereafter positioning the first marker element the first predetermined distance from said third marker element.

6. The method claimed in claim 5 wherein marking said support body at said second predetermined distance comprises frictionally securing said second marker to said support body at said second predetermined distance from said first marker.

7. The method claimed in claim 4 wherein said first and second marker elements are frictionally secured to said support body, and further including sliding said marker elements along said support body to said first and second support body locations.

* * * * *